United States Patent
Benkert et al.

(10) Patent No.: US 12,329,507 B2
(45) Date of Patent: Jun. 17, 2025

(54) MULTIPLE COIL SENSITIVITY MAPS OF COILS OF A RECEIVER ARRAY OF A MAGNETIC RESONANCE IMAGING APPARATUS AND SENSE RECONSTRUCTION

(71) Applicant: Siemens Healthcare GmbH, Erlangen (DE)

(72) Inventors: Thomas Benkert, Neunkirchen am Brand (DE); Marcel Nickel Dominik, Herzogenaurach (DE)

(73) Assignee: Siemens Healthineers AG, Erlangen (DE)

( * ) Notice: Subject to any disclaimer, the term of this patent is extended or adjusted under 35 U.S.C. 154(b) by 139 days.

(21) Appl. No.: 18/134,197

(22) Filed: Apr. 13, 2023

(65) Prior Publication Data

US 2023/0337932 A1 Oct. 26, 2023

(30) Foreign Application Priority Data

Apr. 25, 2022 (EP) .................................... 22169748

(51) Int. Cl.
| | |
|---|---|
| *G01R 33/3415* | (2006.01) |
| *A61B 5/055* | (2006.01) |
| *G01R 33/48* | (2006.01) |
| *G01R 33/561* | (2006.01) |
| *G06T 5/70* | (2024.01) |

(52) U.S. Cl.
CPC .......... *A61B 5/055* (2013.01); *G01R 33/3415* (2013.01); *G01R 33/482* (2013.01); *G01R 33/5611* (2013.01); *G06T 5/70* (2024.01); *G06T 2207/10088* (2013.01)

(58) Field of Classification Search
CPC .. A61B 5/055; G01R 33/3415; G01R 33/482; G01R 33/5611; G01R 33/4826; G01R 33/4828; G01R 33/4835; G01R 33/56; G01R 33/5608; G06T 5/70; G06T 2207/10088
See application file for complete search history.

(56) References Cited

U.S. PATENT DOCUMENTS

| | | |
|---|---|---|
| 9,746,538 B2 | 8/2017 | Wang et al. |
| 2015/0054505 A1 | 2/2015 | Wang et al. |
| 2020/0249300 A1* | 8/2020 | Sandino ................. G06N 3/084 |

OTHER PUBLICATIONS

Griswold, Mark A. et al: "Generalized Autocalibrating Partially Parallel Acquisitions (GRAPPA)", Magnetic Resonance in Medicine, vol. 47, pp. 1202-1210, 2002 // DOI: DOI 10.1002/mrm. 10171.

Ma, Jingfei. "Dixon techniques for water and fat imaging." Journal of Magnetic Resonance Imaging: An Official Journal of the International Society for Magnetic Resonance in Medicine 28.3 (2008): 543-558.; 2008.

(Continued)

*Primary Examiner* — Rishi R Patel
(74) *Attorney, Agent, or Firm* — Banner & Witcoff Ltd.

(57) ABSTRACT

Various examples relate to SENSitivity Encoding (SENSE) reconstruction of Magnetic Resonance Imaging (MRI) images. Multiple coil sensitivity maps per coil of a receiver coil array are used, e.g., obtained from an Eigenvalue-based Spatially Constrained Iterative Reconstruction Technique (ESPIRIT) autocalibration protocol.

14 Claims, 3 Drawing Sheets

(56) References Cited

OTHER PUBLICATIONS

Peters, D. C. et al., "Undersampled projection reconstruction applied to MR angiography", Mag Reson Med;43:91-101, 2000.
Hammernik, Kerstin et al.: "Learning a Variational Network for Reconstruction of Accelerated MRI Data"; in: Magnetic Resonance in Medicine; vol. 79; pp. 3055-3071; 2018; DOI 10.1002/mrm.26977.
Uecker, Martin et al: "ESPIRiT—An Eigenvalue Approach to Autocalibrating Parallel MRI: Where Sense Meets GRAPPA"; in Magnetic Resonance in Medicine; vol. 71; pp. 990-1001; 2014. https://pubmed.ncbi.nlm.nih.gov/23649942/.
Barth, Markus et al: "Simultaneous Multislice (SMS) Imaging Techniques: SMS Imaging"; Magnetic Resonance in Medicine., Bd. 75, Nr. 1, Aug. 26, 2015 (Aug. 26, 2015), pp. 63-81, XP055408927, US ISSN: 0740-31.
Sen Jia et al: "Resolving Fold-Over Artefacts for Reduced Field of-View Parallel Imaging with Cartesian Sampling", Proceedings of the 2021 ISMRM & SMRT Annual Meeting & Exhibition, May 15-20, 2021, ISMRM, 2030 Addison Street, 7th Floor, Berkeley, CA 94704 USA, No. 1164, Apr. 30, 2021 (Apr. 30, 2021), XP040723183.
Qiu Zhilang et al: "Reduced Field of View 1-15 Parallel Imaging with Wave Encoded k-Space Trajectory", Proceedings of the 2021 ISMRM & SMRT Annual Meeting & Exhibition, May 15-20, 2021, ISMRM, 2030 Addison Street, 7th Floor, Berkeley, CA 94704 USA, No. 1154, Apr. 30, 2021 (Apr. 30, 2021), XP040723173.
Sandino C.M. et al: "Accelerating Cardiac Cine MRI Using A Deep Learning-Based ESPIRiT Reconstruction" Magn Reson Med. 2020; 85: 152-167. https://doi.org/10.1002/mrm.28420.
Setsompop, Kawin, et al. "Blipped Controlled Aliasing in Parallel Imaging for Simultaneous Multislice Echo Planar Imaging with Reduced G-Factor Penalty", Magnetic resonance in medicine 67.5 (2012): 1210-1224.
Pruessmann, Klaas P. et al. "SENSE: Sensitivity encoding for fast MRI" Magnetic Resonance in Medicine, vol. 42, No. 5, pp. 952-962, Nov. 1999 (First published: Oct. 28, 1999) // https://doi.org/10.1002/(SICI)1522-2594 (199911)42:5<952::AID-MRM16>3.0.CO;2-S.

* cited by examiner

MULTIPLE COIL SENSITIVITY MAPS OF COILS OF A RECEIVER ARRAY OF A MAGNETIC RESONANCE IMAGING APPARATUS AND SENSE RECONSTRUCTION

CROSS-REFERENCE TO RELATED APPLICATIONS

The present application claims priority to and the benefit of Europe patent application no. EP 22169748.5, filed on Apr. 25, 2022, the contents of which are incorporated herein by reference in their entirety.

TECHNICAL FIELD

The disclosure generally relates to the reconstruction of Magnetic resonance Imaging (MRI) images based on undersampled MRI measurement datasets obtained for multiple coils of a receiver coil array. More particularly, the disclosure relates to employing an image-domain reconstruction that uses multiple coil sensitivity maps per receiver coil.

BACKGROUND

MRI is based on the excitation and detection of the dynamics of nuclear magnetization in a region under examination of an examination object, for example of a patient. The dynamics of the nuclear magnetization has frequencies in the radio-frequency (RF) spectrum. With conventional MRI techniques, the spatial frequency domain (also called k-space) is sampled by acquiring raw MRI data. With a sufficiently dense sampling (as given e.g. to avoid aliasing artifacts by the so-called Nyquist criterion) of the spatial frequency domain, an MRI image can be created in the image domain by Fourier transformation of the MRI raw data. Dense sampling in this context can be understood to refer to a sampling with sufficient density to satisfy the Nyquist criterion, whereas undersampling refers to a sampling with a lower density than stipulated by the Nyquist criterion.

Different techniques are known for reducing the time duration (acquisition time) needed for MRI. One technique is parallel imaging or partial parallel acquisition (PPA).

Parallel imaging aims to reconstruct MR images from an undersampled multi-channel k-space dataset. That is, the multi-channel k-space dataset includes multiple k-space data acquired using different coils of a receiver coil array.

In most cases, the main motivation for this is to reduce acquisition time as fewer k-space data is sampled. The reconstruction of the MR image is based on a signal model that uses information of the different channels to effectively increase the sampling density. This allows to reconstruct a larger field-of-view and/or to avoid aliasing artifacts. In other words, an undersampling trajectory is used that samples k-space data in the k-space, however, below the Nyquist limit with respect to the field-of-view (so that aliasing artifacts would normally occur).

One of the most prominent approaches for the reconstruction is SENSE. See Pruessmann KP, Weiger M, Scheidegger MB, Boesiger P. "SENSE: sensitivity encoding for fast MRI." Magn Reson Med. 1999 November;42 (5): 952-62. PMID: 10542355. The SENSitivity Encoding (SENSE) reconstruction algorithm exploits that the image for each receive channel is given by the product of a highly resolved image and a smooth coil sensitivity map (CSM). In its original formulation, the SENSE reconstruction algorithm was used for regular undersampling patterns, i.e. two-dimensional (2-D) Cartesian undersampling trajectories, so that the reconstruction could be performed purely in the image domain. For this purpose, the undersampled k-space data for each coil of the receiver coil array was Fourier transformed into a respective aliased channel image, and each one of aliased channel images was unfolded by use of the precalculated CSMs. The approach was extended to arbitrary Cartesian k-space trajectories and to non-Cartesian k-space trajectories. In this general formulation, the model directly relates the sampled k-space data to the reconstructed image. The calculation is typically done iteratively using an iterative optimization. All such approaches are referred to as SENSE reconstruction.

SENSE reconstruction is known to be more sensitive to aliasing. This is, in particular, true when compared to k-space-based reconstruction, such as GRAPPA reconstruction. See Griswold, Mark A., et al. "Generalized autocalibrating partially parallel acquisitions (GRAPPA)." Magnetic Resonance in Medicine: An Official Journal of the International Society for Magnetic Resonance in Medicine 47.6 (2002): 1202-1210. In particular, the SENSE reconstruction is prone to wrap-around artifacts. Also, see US20150054505A1.

In the article of Jia et al., "Resolving fold-over artefacts for Reduced Field-of-View Parallel Imaging with Cartesian Sampling", Proc. Int. Soc. Magn. Reson. Med. S. 1164, 2021, a method to resolve fold-over artefacts is disclosed.

SUMMARY

Accordingly, a need exists to improve the techniques of SENSE reconstruction. Specifically, a need exists for techniques that reduce aliasing and wrap-around artifacts. This need is met by the embodiments as discussed herein, including the features of the claims.

A computer-implemented method of reconstructing MRI images includes, for each coil of a receiver coil array of an MRI apparatus, determining a respective set of two or more coil sensitivity maps using an autocalibration protocol such as an ESPIRIT autocalibration protocol. The autocalibration protocol densely samples a part of the k-space. The method also includes, for each coil of the receiver coil array, determining a respective coil sensitivity data structure comprising the respective two or more coil sensitivity maps in a stitched arrangement along a given direction in the k-space. A stitching factor of the stitched arrangement corresponds to the count of the two or more coil sensitivity maps of the respective set. The method further includes, for each coil of the receiver coil array, acquiring k-space data using an undersampling trajectory in the k-space and determining a respective measurement data structure. Each respective measurement data structure comprises the respective k-space data rearranged in the k-space on an adjusted k-space trajectory that is determined by stretching the k-space trajectory by the stitching factor along the given direction. The method further includes, based on the coil sensitivity data structures determined for the coils of the receiver coil array and further based on the measurement data structures determined for the coils of the receiver coil array, performing an iterative optimization based on a SENSE reconstruction algorithm to obtain at least one MRI image. The iterative optimization comprises, for at least some iterations of multiple iterations of the iterative optimization, a regularization operation and a data-consistency operation. The data-consistency operation is based on differences between the measurement data structures and respective synthesized measurement data structures, the synthesized MRI measurement data structures being based on a k-space representation of at least one prior MRI image of the multiple iterations and the adjusted undersampling trajectory and the coil sensitivity data structures.

A computer program or a computer-program product includes program code. The program code can be loaded and executed by at least one processor. The at least one processor, upon executing the program code, performs a method of reconstructing MRI images. The method includes, for each coil of a receiver coil array of an MRI apparatus, determining a respective set of two or more coil sensitivity maps using an autocalibration protocol such as an ESPIRIT autocalibration protocol. The autocalibration protocol densely samples a part of the k-space. The method also includes, for each coil of the receiver coil array, determining a respective coil sensitivity data structure comprising the respective two or more coil sensitivity maps in a stitched arrangement along a given direction in the k-space. A stitching factor of the stitched arrangement corresponds to the count of the two or more coil sensitivity maps of the respective set. The method further includes, for each coil of the receiver coil array, acquiring k-space data using an undersampling trajectory in the k-space and determining a respective measurement data structure. Each respective measurement data structure comprises the respective k-space data rearranged in the k-space on an adjusted k-space trajectory that is determined by stretching the k-space trajectory by the stitching factor along the given direction. The method further includes, based on the coil sensitivity data structures determined for the coils of the receiver coil array and further based on the measurement data structures determined for the coils of the receiver coil array, performing an iterative optimization based on a SENSE reconstruction algorithm to obtain at least one MRI image. The iterative optimization comprises, for at least some iterations of multiple iterations of the iterative optimization, a regularization operation and a data-consistency operation. The data-consistency operation is based on differences between the measurement data structures and respective synthesized measurement data structures, the synthesized MRI measurement data structures being based on a k-space representation of at least one prior MRI image of the multiple iterations and the adjusted undersampling trajectory and the coil sensitivity data structures.

Thus, in an embodiment the computer program may be stored on any suitable non-transitory computer-readable medium, and may comprise program code configured to be executed by at least one processor. The at least one processor, upon executing the program code, may perform any of the computer-implemented methods as described herein, including those described in the claims.

A device comprises at least one processor and a memory. The at least one processor is configured to load program code from the memory and to execute the program code from the memory. Upon executing the program code from the memory, the at least one processor performs a method of reconstructing MRI images. The method includes, for each coil of a receiver coil array of an MRI apparatus, determining a respective set of two or more coil sensitivity maps using an autocalibration protocol such as an ESPIRIT autocalibration protocol. The autocalibration protocol densely samples a part of the k-space. The method also includes, for each coil of the receiver coil array, determining a respective coil sensitivity data structure comprising the respective two or more coil sensitivity maps in a stitched arrangement along a given direction in the k-space. A stitching factor of the stitched arrangement corresponds to the count of the two or more coil sensitivity maps of the respective set. The method further includes, for each coil of the receiver coil array, acquiring k-space data using an undersampling trajectory in the k-space and determining a respective measurement data structure. Each respective measurement data structure comprises the respective k-space data rearranged in the k-space on an adjusted k-space trajectory that is determined by stretching the k-space trajectory by the stitching factor along the given direction. The method further includes, based on the coil sensitivity data structures determined for the coils of the receiver coil array and further based on the measurement data structures determined for the coils of the receiver coil array, performing an iterative optimization based on a SENSE reconstruction algorithm to obtain at least one MRI image. The iterative optimization comprises, for at least some iterations of multiple iterations of the iterative optimization, a regularization operation and a data-consistency operation. The data-consistency operation is based on differences between the measurement data structures and respective synthesized measurement data structures, the synthesized MRI measurement data structures being based on a k-space representation of at least one prior MRI image of the multiple iterations and the adjusted undersampling trajectory and the coil sensitivity data structures.

A computer-implemented method of reconstructing MRI images includes, for each coil of a receiver coil array of an MRI apparatus, determining a respective coil sensitivity map using an autocalibration protocol such as an ESPIRIT autocalibration protocol densely sampling a part of the k-space for a first field-of-view. The computer-implemented method further includes, for each coil of the receiver coil array of the MRI apparatus, acquiring k-space data using an undersampling trajectory in the k-space for a second field-of-view that is an integer fraction of the first field-of-view and determining a respective measurement data structure comprising the respective k-space data rearranged in the k-space on an adjusted k-space trajectory that is determined by stretching the k-space trajectory by the inverse of the integer fraction. The computer-implemented method further includes, based on the coil sensitivity maps determined for the coils of the receiver coil array and further based on the measurement data structures determined for the coils of the receiver coil array, performing an iterative optimization based on a SENSE reconstruction algorithm to obtain at least one MRI image. The iterative optimization comprises, for at least some iterations of multiple iterations of the iterative optimization, a regularization operation and a data-consistency operation to obtain respective current MRI images. The data-consistency operation is based on differences between the measurement data structures and respective synthesized measurement data structures, the synthesized MRI measurement data structures being based on a k-space representation of at least one prior MRI image of the multiple iterations and the adjusted undersampling trajectory and the coil sensitivity data structures.

A computer program or a computer-program product includes program code. The program code can be loaded and executed by at least one processor. The at least one processor, upon executing the program code, performs a method of reconstructing MRI images. The method includes, for each coil of a receiver coil array of an MRI apparatus, determining a respective coil sensitivity map using an autocalibration protocol such as an ESPIRIT autocalibration protocol densely sampling a part of the k-space for a first field-of-view. The computer-implemented method further includes, for each coil of the receiver coil array of the MRI apparatus, acquiring k-space data using an undersampling trajectory in the k-space for a second field-of-view that is an integer fraction of the first field-of-view and determining a respective measurement data structure comprising the respective k-space data rearranged in the k-space on an adjusted k-space trajectory that is determined by stretching the k-space trajectory by the inverse of the integer fraction. The computer-implemented method further includes, based on the coil sensitivity maps determined for the coils of the receiver coil array and further based on the measurement data structures determined for the coils of the receiver coil array, performing an iterative optimization based on a SENSE reconstruction algorithm to obtain at least one MRI image. The iterative optimization comprises, for at least some iterations of multiple iterations of the iterative optimization, a regularization operation and a data-consistency operation to obtain respective current MRI images. The data-consistency operation is based on differences between the measurement data structures and respective synthesized measurement data structures, the synthesized MRI measurement data structures being based on a k-space representation of at least one prior MRI image of the multiple iterations and the adjusted undersampling trajectory and the coil sensitivity data structures.

A device comprises at least one processor and a memory. The at least one processor is configured to load program code from the memory and to execute the program code from the memory. Upon executing the program code from the memory, the at least one processor performs a method of reconstructing MRI images. The method includes, determining a respective coil sensitivity map using an autocalibration protocol such as an ESPIRIT autocalibration protocol densely sampling a part of the k-space for a first field-of-view. The computer-implemented method further includes, for each coil of the receiver coil array of the MRI apparatus, acquiring k-space data using an undersampling trajectory in the k-space for a second field-of-view that is an integer fraction of the first field-of-view and determining a respective measurement data structure comprising the respective k-space data rearranged in the k-space on an adjusted k-space trajectory that is determined by stretching the k-space trajectory by the inverse of the integer fraction. The computer-implemented method further includes, based on the coil sensitivity maps determined for the coils of the receiver coil array and further based on the measurement data structures determined for the coils of the receiver coil array, performing an iterative optimization based on a SENSE reconstruction algorithm to obtain at least one MRI image. The iterative optimization comprises, for at least some iterations of multiple iterations of the iterative optimization, a regularization operation and a data-consistency operation to obtain respective current MRI images. The data-consistency operation is based on differences between the measurement data structures and respective synthesized measurement data structures, the synthesized MRI measurement data structures being based on a k-space representation of at least one prior MRI image of the multiple iterations and the adjusted undersampling trajectory and the coil sensitivity data structures.

It is to be understood that the features mentioned above and those yet to be explained below may be used not only in the respective combinations indicated, but also in other combinations or in isolation without departing from the scope of the disclosure.

BRIEF DESCRIPTION OF THE DRAWINGS

Further advantages, features, and details of the disclosure appear in the exemplary embodiments described herein and with reference to the drawings, in which.

DETAILED DESCRIPTION OF THE DISCLOSURE

Figure 1:
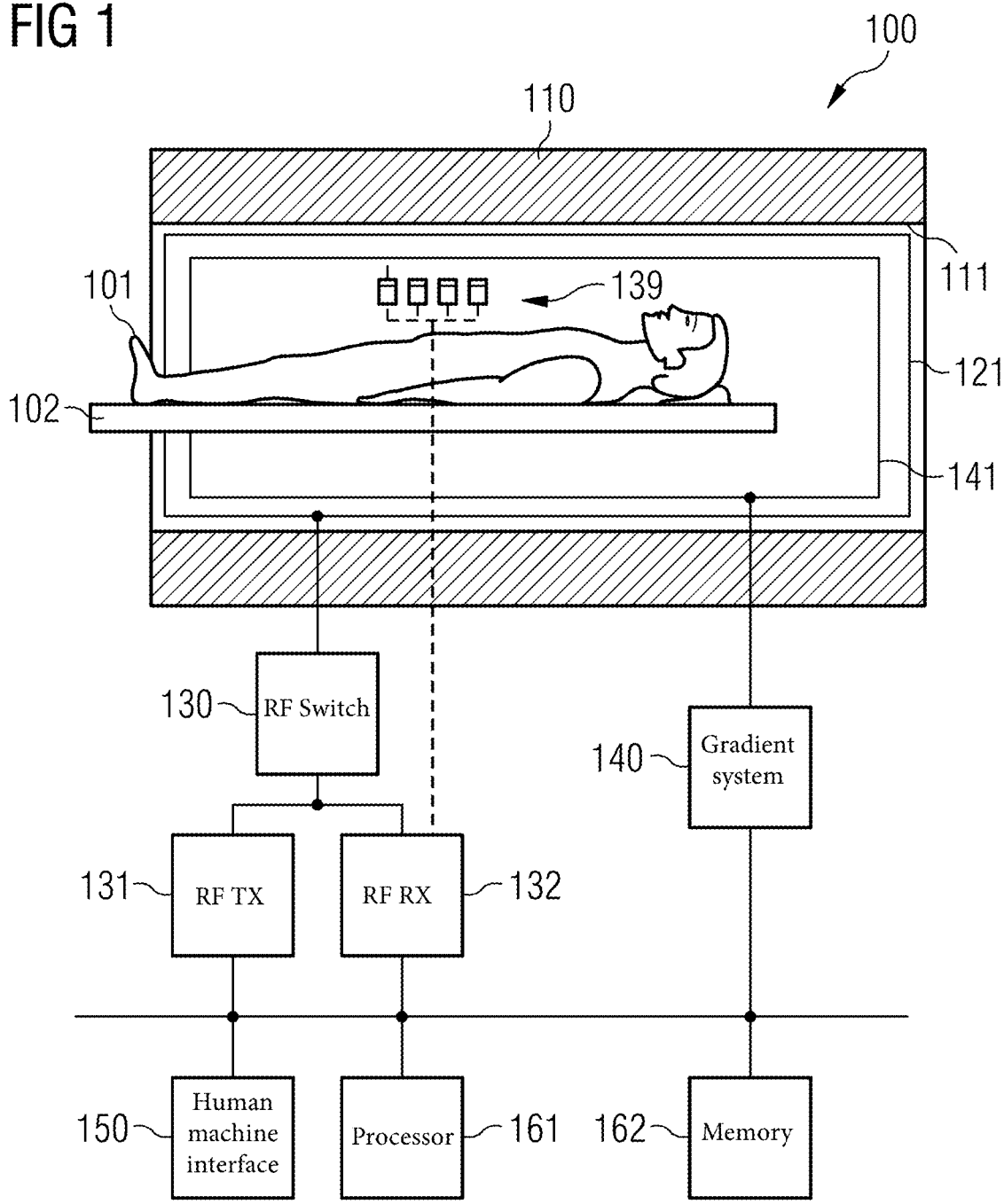
FIG. 1 schematically illustrates an example MRI apparatus according to various embodiments of the present disclosure.

Some examples of the present disclosure generally provide for a plurality of circuits or other electrical devices. All references to the circuits and other electrical devices, and the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any suitable circuit or other suitable electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the disclosure will be described in detail with reference to the accompanying drawings. It is to be understood that the following description of embodiments is not to be taken in a limiting sense. The scope of the disclosure is not intended to be limited by the embodiments described hereinafter or by the drawings, which are taken to be illustrative and not limiting.

The drawings are to be regarded as being schematic representations and elements illustrated in the drawings are not necessarily shown to scale. Rather, the various elements are represented such that their function and their general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various techniques described herein generally relate to MRI. MRI k-space data (or raw data) is acquired in k-space by sampling k-space. Parallel imaging can be applied. Here, MRI data is acquired using an array of receiver coils each having a predefined spatial sensitivity. A multi-channel MRI measurement dataset is obtained that includes a set of k-space data, for each coil. The set of k-space data (MRI measurement dataset) is sparsely sampled in k-space, i.e., MRI data is acquired below the Nyquist threshold for a given field of view. This is sometimes referred to as undersampling k-space. According to various embodiments, the MRI measurement datasets may be obtained using an undersampling trajectory. When acquiring MRI measurement datasets using an undersampling trajectory for certain k-space locations, raw MRI data is not sampled and the missing information is subsequently reconstructed. A so-called "acceleration factor" is indicative of the fraction of those k-space locations along the undersampling trajectory for which no raw data samples are acquired. Larger (smaller) acceleration factors may result in a shorter (longer) scan times.

Then, MRI reconstruction is employed to reconstruct an MRI image (reconstructed MRI image) without or at least with reduced aliasing artifacts. The MRI reconstruction often relies on predetermined or calibrated coil sensitivity maps (CSMs) of multiple receiver coils of the RF receiver of the MRI apparatus. This is a so-called SENSE reconstruction in image domain. An iterative optimization is used. The iterative optimization aims to minimize or maximize a goal function (albeit this can be implicitly implemented where a deep-learning reconstruction is used). The iterative optimization includes, for at least some iterations of multiple iterations of the iterative optimization, a regularization operation and a data-consistency operation. The data-consistency operation is based on differences between the measurement data and respective synthesized measurement data, the synthesized MRI measurement data being based on a k-space representation of at least one prior MRI image of the multiple iteration, CSMs, and the sampling pattern in k-space, i.e., the k-space trajectory. Further, an appropriate optimization technique, for example a gradient descent optimization technique or Landweber iterations, or prima-dual method, or alternating direction method of multipliers as known in the art, may be used to optimize parameters from iteration to iteration, i.e., to minimize the goal function including the regularization operator and the data-consistency operator. The data-consistency operation can be based on the squared $l_2$-norm of the difference between measured data and synthesized data using the signal model. A gradient can be considered in accordance with the optimization technique. For instance, for decorrelated data with Gaussian noise this can be a good choice. The data-consistency operator can employ e.g., for a gradient-descent type formulation of the optimization, forward and backward operators, translating between the MRI measurement data and the reconstructed MRI images, respectively. The regularization operation may be implemented using a total variation approach or using multiple layers of a convolutional neural network, see Hammernik, Kerstin, et al. "Learning a variational network for reconstruction of accelerated MRI data." *Magnetic resonance in medicine* 79.6 (2018): 3055-3071.

On the other hand, GRAPPA reconstruction does not require CSMs. Rather, a densely sampled section of the k-space, at the center of the k-space, is used for reconstruction of missing points in the k-space.

Uecker M, Lai P, Murphy MJ, Virtue P, Elad M, Pauly JM, Vasanawala SS, Lustig M. "ESPIRIT-an eigenvalue approach to autocalibrating parallel MRI: where SENSE meets GRAPPA." Magn Reson Med. 2014 March;71 (3): 990-1001 describes that SENSE and GRAPPA reconstruction can be related when sets of multiple CSMs are considered per coil. That is, per coil, multiple CSMs are determined. For practical purposes, two CSMs per coil are used. These sets of CSMs per coil can be determined using the ESPIRIT autocalibration protocol, based on a densely-sampled part of the k-space for a given field-of-view (FOV).

The Eigenvalue-based Spatially Constrained Iterative Reconstruction Technique (ESPIRIT) autocalibration protocol can not only be used to determine multiple CSMs per coil, but also for reconstruction. See, e.g., Sandino, CM, Lai, P, Vasanawala, SS, Cheng, JY. "Accelerating cardiac cine MRI using a deep learning-based ESPIRIT reconstruction." Magn Reson Med. 2020; 85:152-167. Here, a neural network algorithm (neural network) is used for reconstruction. The use of multiple sets of CSMs is directly embedded into the network architecture of the neural network. Therefore, implementation of this reconstruction requires a dedicated reconstruction algorithm, dedicated training of the neural network, etc. This poses significant practical challenges, e.g., where a SENSE reconstruction is previously employed.

Hereinafter, techniques are disclosed that employ a set of CSMs per coil, determined using an autocalibration protocol such as the ESPIRIT autocalibration protocol, as input data to a SENSE reconstruction algorithm.

The autocalibration protocol densely samples a part of the k-space, e.g., at its center, for a given FOV. The k-space data for reconstruction is acquired using an undersampling trajectory, e.g., for the same FOV. Then, the sets of CSMs per coil include a first order CSM that includes features within the FOV and a second order CSM that includes wrap-in information from outside the FOV. This means that CSMs of rank larger than one are used in an image-domain reconstruction of rank equal to one.

For example, a trained deep-learning SENSE reconstruction can be used. Here, a regularization operation of an iterative optimization is implemented using layers of a convolutional neural network.

The SENSE reconstruction algorithm is not required to be modified if compared to prior-art implementations where only a single CSM per coil is used. This means that, e.g., the convolutional neural network is not required to be specifically adapted or trained, as would be the case in Sandino et al.

To achieve this, it is possible to acquire, for each coil of the receiver coil array of the MRI apparatus, k-space data using an undersampling trajectory in k-space and then to determine a respective measurement data structure. The measurement data structure of each coil includes the respective k-space data rearranged in k-space on an adjusted k-space trajectory that is determined by stretching the k-space trajectory by a certain factor along a given direction.

This certain factor ("stitching factor") is determined by the count of CSMs. For instance, the stitching factor could be two, if per coil a set of two CSMs is considered.

Next, it is explained why the factor by which the adjusted k-space trajectory is stretched with respect to the original k-space trajectory used for measurement is labeled a "stitching factor".

Specifically, it is possible to determine, for each coil, a respective coil sensitivity data structure that includes the respective CSMs of that set in a stitched arrangement, i.e., stacked next to each other. The stitching is along the given direction in the k-space. Thus, where two CSMs per coil are available, the coil sensitivity data structure includes those two CSMs arranged next to each other along the given direction.

Thereby, a SENSE reconstruction algorithm can be used that is configured to accept, as input data, the coil sensitivity data structures of the multiple coils and the measurement data structures of the multiple coils for a varying, predetermined range of stitching factors.

For example, stitching factors between 1 (no stitching, original data) and at least 5 (5 CSMs per coil) could be accepted.

Specifically, a conventional SENSE reconstruction algorithm can be reused that is configured to also accept, as the input data, non-stitched CSMs (i.e., a single CSM per coil) in the k-space data that is not rearranged in the k-space, i.e., a conventional measurement data set.

As will be appreciated, only the dimension of the data structures along the given direction may vary for varying stitching factors.

Such a varying dimension (i.e., non-stitched CSM, stitched CSM with varying stitching factors) can be natively handled by the SENSE reconstruction algorithm, e.g., by simply extending summation and/or convolutions in this direction. This finding is further explained below.

The ESPIRIT signal model assumes that the coil images are modeled as:

$$S_I(x) = \Sigma_{s=1}^{S} C_I^{(S)}(x) M^{(s)}(x) \quad (1)$$

where S represents the number of CSMs per coil, I represents the channel index, $S_I(x)$ represents the coil image at index x, $C_I^{(S)}(x)$ represents the estimated CSM from the autocalibration protocol and $M^{(s)}(x)$ represents the image of each CSM.

The reconstructed MRI images are obtained by finding the minimum of the cost function (target function of the iterative optimization):

$$\chi^2 = \Sigma_{k,I} |(PUS_I)(k) - D_I(k)|^2 \quad (2)$$

where k samples the acquired k-space indices, P projects on such indices, U represents the Fourier Transformation, and $D_I(k)$ represents the acquired k-space data.

The conventional SENSE reconstruction algorithm operates based on S=1 in Eq. (1).

Compressed Sensing approaches often start with a cost function that is iteratively optimized. In that case, one term in the cost function that relates the images to the acquired data is given by Eq. (2).

Deep learning reconstructions that involve data consistency based on the SENSE/ESPIRIT signal model, such as unrolled networks or variational networks, involve a data consistency update of the reconstructed image based on a gradient of the function in Eq. (2) with respect to the images.

The ESPIRIT signal model is a superposition of S images and aims to unwrap the field-of-view by this factor. In other words, the k-space is S times more refined.

Next, it is assumed that the undersampling trajectory, defined by the measurement protocol using excitation pulses and gradients, etc., includes sampling points arranged on a Cartesian pattern in the k-space along the given direction (i.e., along the stacking direction). This would be the case for line-wise Cartesian sampling (full Cartesian sampling), but also k-space trajectories that include sampling points arranged in a non-Cartesian pattern along one or more further directions perpendicular to the given direction. Examples would be stack-of-stars or stack-of-spirals patterns, see, e.g., Peters DC, Korosec FR, Grist TM, Block WF, Holden JE, Vigen KK, Mistretta CA. "Undersampled projection reconstruction applied to MR angiography." Magn Reson Med 2000; 43:91-10; and Deng W, Zahneisen B, Stenger VA. "Rotated stack-of-spirals partial acquisition for rapid volumetric parallel MRI." Magn Reson Med 2016; 76:127-135.

For ease of explanation, the given direction along which the stitching is applied is assumed to correspond to the phase-encoding direction of the underlying measurement protocol. However, it would also be possible that the given direction is, e.g., the readout direction.

It is assumed that the space index x ∈ [0, N−1). Now, the stitching in image space is defined by:

$$\tilde{A}(x) = \begin{cases} A^{(1)}(x \bmod N), & 0 \leq x < N \\ \vdots \\ A^{(s)}(x \bmod N), & N \leq x < sN, \\ \vdots \\ A^{(S)}(x \bmod N), & (S-1)N \leq x < SN \end{cases} \quad (3)$$

where $A(x) \in \{C_I^S(x), M^{(S)}(x)\}$.

Given the Fourier transform Ũ for the given direction/stitched dimension, one obtains:

$$\tilde{a}(k) = \sum_{x=0}^{SN-1} \tilde{u}_{kx} \tilde{A}(x) = \sum_{x=0}^{SN-1} e^{-\frac{2\pi i}{SN} kx} \tilde{A}(x) \quad (4)$$

So, if every S-th line is downsampled to a Fourier transformation (using the periodicity), one gets:

$$a(k) = \tilde{a}(Sk) = = \sum_{x=0}^{SN-1} e^{-\frac{2\pi i}{N} kx} \tilde{A}(x) = = \sum_{x=0}^{N-1} e^{-\frac{2\pi i}{N} kx} \sum_{s=1}^{S} A^{(s)}(x) \quad (5)$$

This means that the subsampled Fourier transform on the stitched images gives the aliased images. This explains why the stitching makes it possible to re-use a conventional SENSE reconstruction algorithm without modifications thereto.

According to various examples, this approach can be extended for water-fat separation based on the Dixon method. See, e.g., Ma, Jingfei. "Dixon techniques for water and fat imaging." Journal of Magnetic Resonance Imaging: An Official Journal of the International Society for Magnetic Resonance in Medicine 28.3 (2008): 543-558.

Generally, the time evolution of MRI signals captured by the MRI data associated with different spin species exhibit different phase offsets at different echo times, due to the chemical shift. This effect can be exploited to separate the MRI signals and determine respective MRI images, i.e., for different spin species at the multiple slices simultaneously acquired.

For Dixon separation of multiple spin species, multiple different contrasts E are acquired at multiple echo times and different chemical species associated with different, a priori known spectral profiles are separated. That is, multiple reconstructed MRI images are obtained for different spin species. Typically, water and fat species are separated.

The echo time in this context refers to a time offset relative to a timepoint for which water and fat, or generally the different spin species, are aligned, i.e., the magnetization points into the same direction. For example, for spin-echo sequences, such time offset can also take negative values. In this case, the contrast refers to a timepoint before refocusing water and fat signals are aligned.

For water-fat separation, a water MRI image can be determined having a contrast that is affected by water spins (but not, or only to a limited degree, by fat spins); and a fat MRI image can be determined having a contrast that is affected by fat spins (but not, or only to a limited degree, by water spins).

According to reference implementations, for Dixon separation, a signal model is used that models the MRI signals based on various physical parameters such as the water and fat contribution to a respective pixel/voxel (hereinafter, the term "pixel" is intended to embrace 3-D structures such as voxels). These physical parameters can, depending on the complexity of the signal model, encompass additional properties of the measurement system, specifically various imperfections affecting the reference value of the phase (simply, reference phase). A respective phase map can be considered. The phase map of the signal model can describe the spatial evolution of the reference phase of the MRI data due to the polarizing magnetic field being inhomogeneous and/or due to use of bipolar readout gradient fields of the measurement protocol used for creating gradient echoes at the multiple echo times.

The signal model can be fitted to the time evolution of the MRI data, thereby finding parameter values for the physical parameters, and specifically separating water and fat contributions to the MRI signal.

The signal model can be considered as part of the data-consistency operation in the iterative optimization for reconstruction.

For a given coil I and contrast e, the SENSE signal model is given by $$S_{I,e} = \Sigma_{K=1}^{K} C_I(x) \Phi_e(x) C_{e,k} M_k(x), \quad (6)$$

where $\Phi_e(x)$ represents the overall phase evolution (in particular frequency offsets, eddy current effects and gradient delays) and $c_{e,k}$ represents the spectral dephasing at the echo time $T_e$ of the respective eth echo for the kth chemical component, i.e., relative dephasing between the spin species. For water-fat separation: $M_1(x)=W(x)$ as water, $M_2(x)=F(x)$ as fat, $C_{e,1}=1$ and abbreviate $C_{e,2}=C_e$. This gives:

$$S_{I,e}(x) = C_I(x)(W(x) + c_e F(x)) \Phi_e(x). \quad (7)$$

Looking at Eq. (6) and assuming that $C_1(x)$, $\Phi_e(x)$ and $C_{e,k}$ are known from previous processing (CSM, initial Dixon reconstruction; note that these maps are usually assumed to be spatially smooth), it is possible to map the two indices (I,e) onto a one-dimensional index. With a mapping of the form:

$$(I,e) \rightarrow I,$$

$$C_I(x) \Phi_e(x) c_{e,k} \rightarrow C_I(x), \quad (8)$$

Introducing effective coils for each chemical species, the Dixon signal model in Eq. (6) looks like Eq. (1). Consequently, if the same mapping for the indices (I,e) is applied to the k-space data, a model based Dixon reconstruction can be performed using a reconstruction algorithm based on SENSE.

Eq. (8) corresponds to augmenting the respective coil sensitivity data structure by combining the respective coil sensitivity data structure with predetermined dephasing maps $\Phi_e(x)$ obtained for each one of the multiple echo times and at least one predetermined dephasing factor $c_{e,k}$ associated with a relative dephasing between at least one pair of the two or more spin species.

Thus, it is even possible to re-use the conventional SENSE reconstruction algorithm for DIXON separation where the bookkeeping of the respective information of the phase maps and the dephasing is managed by the coil sensitivity data structures (these coil sensitivity data structures then include information beyond the CSMs).

FIG. 1 schematically illustrates an example MRI apparatus according to various embodiments of the present disclosure. FIG. 1 depicts aspects with respect to an MRI apparatus 100. The MRI apparatus 100 includes a magnet 110, which defines a bore 111. The magnet 110 may provide a DC magnetic field of one to six Tesla along its longitudinal axis. The DC magnetic field may align the magnetization of the patient 101 along the longitudinal axis. The patient 101 may be moved into the bore by means of a movable table 102.

The MRI apparatus 100 also includes a gradient system 140 for creating spatially-varying magnetic gradient fields (gradients) used for spatially encoding MRI data. Typically, the gradient system 140 includes at least three gradient coils 141 that are arranged orthogonal to each other and may be controlled individually. By applying gradient pulses to the gradient coils 141, it is possible to apply gradients along certain directions. The gradients may be used for slice selection (slice-selection gradients), frequency encoding (readout gradients), and phase encoding along one or more phase-encoding directions (phase-encoding gradients). The directions along which the various gradients are applied are not necessarily in parallel with the axes defined by the coils 141. Rather, it is possible that these directions are defined by a certain k-space trajectory, which, in turn, may be defined by certain requirements of the respective MRI sequence and/or based on anatomic properties of the patient 101. Gradients can also be used for forming gradient echoes. For instance, a gradient pulse train can be used that has gradients of opposing polarity.

For preparation and/or excitation of the magnetization polarized/aligned with the DC magnetic field, RF pulses may be applied. For this, an RF coil assembly 121 is provided which is capable of applying an RF pulse such as an inversion pulse or an excitation pulse or a refocusing pulse (that can address multiple slices for Simultaneous Multi-Slice (SMS)). While the inversion pulse generally inverts the direction of the longitudinal magnetization, excitation pulses may create transversal magnetization.

For creating RF pulses, an RF transmitter 131 is connected via a RF switch 130 with the coil assembly 121. Via a RF receiver 132, it is possible to detect signals of the magnetization relaxing back into the relaxation position aligned with the DC magnetic field. For example, it is possible to detect echoes; echoes may be formed by applying one or more RF pulses (spin echo) and/or by applying one or more gradients (gradient echo). The magnetization may be inductively coupled with the coil assembly 121 for this purpose. Thereby, raw MRI data in k-space is acquired.

Generally, it would be possible to use separate coil assemblies for applying RF pulses on the one hand side and for acquiring MRI data on the other hand side (not shown in FIG. 1).

The MRI apparatus 100 further includes a human machine interface 150, e.g., a screen, a keyboard, a mouse, etc. By means of the human machine interface 150, a user input may be detected and output to the user may be implemented. For example, by means of the human machine interface 150, it is possible to set certain configuration parameters for the MRI sequences to be applied.

The MRI apparatus 100 further includes a processing unit (also referred to as a processor or processing circuitry) 161. The processor 161 may include a GPU and/or a CPU. The processor 161 may implement various control functionality with respect to the operation of the MRI apparatus 100, e.g., based on program code loaded from a memory 162. For example, the processor 161 could implement a sequence control for time-synchronized operation of the gradient system 140, the RF transmitter 131, and the RF receiver 132. The processor 161 may also be configured to implement an MRI reconstruction, i.e., implement reconstruction of MRI images based on MRI measurement datasets; separation of multiple spin species; using a SENSE reconstruction for determining one or more MRI images, etc.

It is not required in all scenarios that processor 161 implements post-processing for reconstruction of the MRI images. In other embodiments, it would be possible that respective functionalities implemented by a separate device, such as the one as illustrated in FIG. 2.

Figure 2:
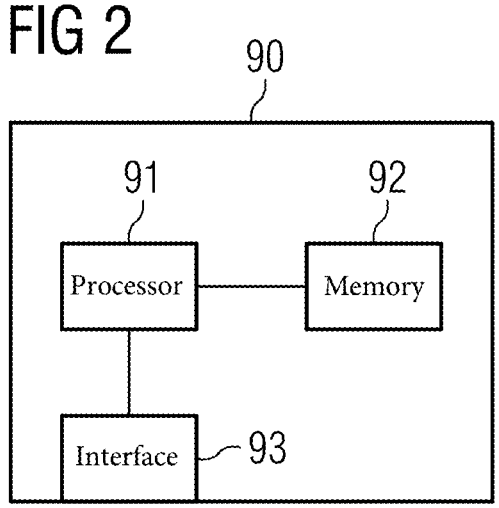
FIG. 2 schematically illustrates an example processing device according to various embodiments of the present disclosure.

FIG. 2 schematically illustrates an example processing device according to various embodiments of the present disclosure. The device 90 includes a processing unit (also referred to as a processor or processing circuitry) 91 and a memory 92. The processor 91 can obtain an MRI measurement dataset including k-space data for multiple receiver coils via an interface 93, e.g., from a hospital database, a computer-readable storage medium, or directly from an MRI apparatus 100 as discussed in connection with FIG. 1. Upon loading program code from the memory 92, the processor 91 can post-process the MRI measurement dataset to reconstruct at least one MRI image, e.g., a single MRI image or multiple MRI images separating spin species. Details with respect to such processing are illustrated in connection with FIG. 3.

Figure 3:
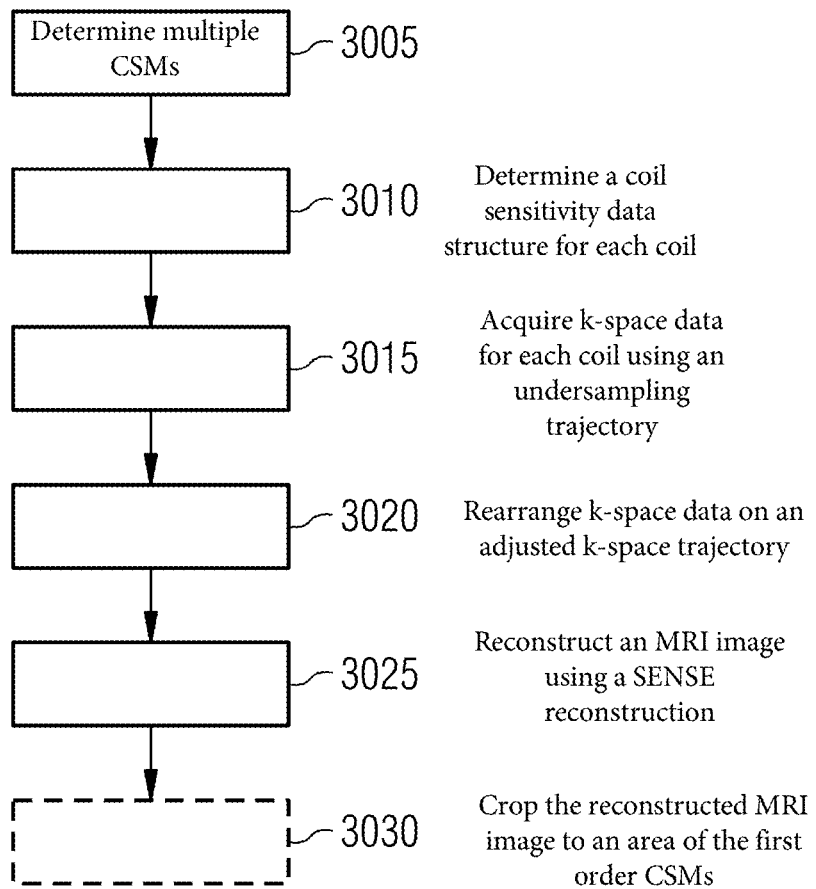
FIG. 3 is a flowchart of an example method according to various embodiments of the present disclosure.

FIG. 3 is a flowchart of an example method according to various embodiments of the present disclosure. The method of FIG. 3 generally pertains to reconstruction of one or more MRI images using an image-domain reconstruction, i.e., a SENSE reconstruction. Multiple CSMs are considered per coil of a receiver coil array. For instance, the method of FIG. 3 could be executed by the processor 161 and/or by the processor 91 (cf. FIG. 1; FIG. 2).

At box 3005, multiple CSMs are determined for each coil of the receiver coil array of the MRI apparatus. These CSMs can be determined using an autocalibration protocol that densely samples a part of the k-space. For example, two CSMs may be determined. Reference techniques available to the skilled person can be used in box 3005, e.g., ESPIRIT autocalibration.

At box 3010, a respective coil sensitivity data structure can be determined for each coil. For instance, if a receiver coil array including four coils (cf. FIG. 1) is used, then a total of four coil sensitivity data structures would be obtained. The CSMs of a given coil are stretched along a given direction in the k-space, for each coil.

It would be possible to shift the coil sensitivity data structure (using wrap-around) in the same direction to adapt a correct convention for the discrete Fourier transformation.

Optionally, it would be possible perform a phase correction for the reference phase (global offset) of the coil sensitivity data structure. This can be done by reference CSMs available on a larger field-of-view.

Next at box 3015, k-space data is acquired for each coil using an undersampling trajectory.

At box 3020, the k-space data is then re-arranged in the k-space on an adjusted k-space trajectory. This adjusted k-space trajectory is determined by stretching the k-space trajectory by the stitching factor along the given direction. This yields a measurement data structure.

Figure 4:
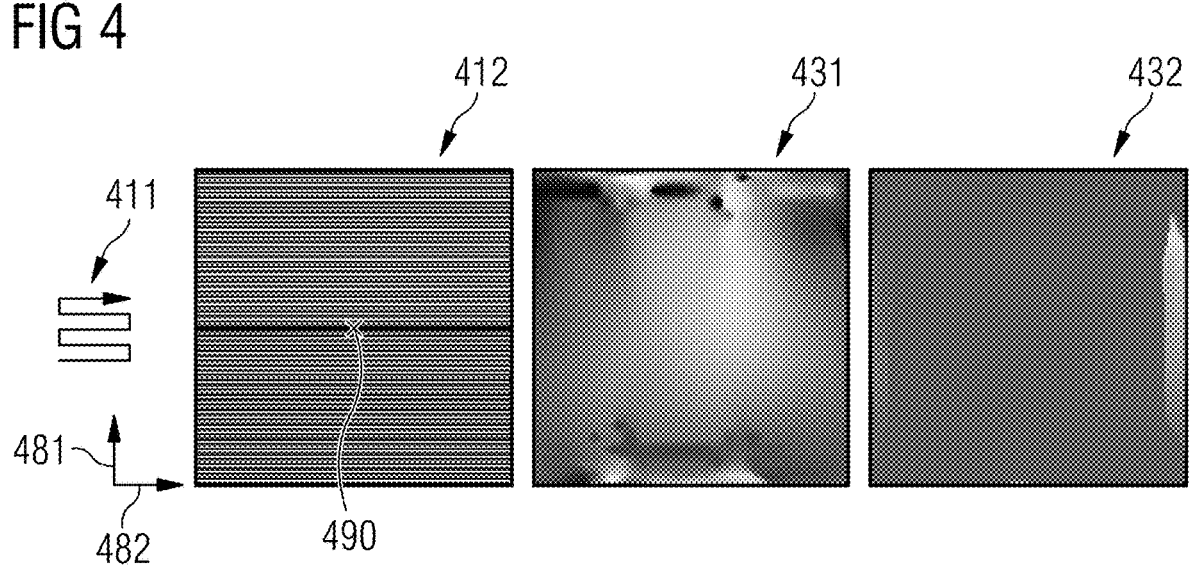
FIG. 4 schematically illustrates example multiple coil sensitivity maps associated with a receiver coil, as well as example k-space data associated with the receiver coil according to various embodiments of the present disclosure.
Figure 5:
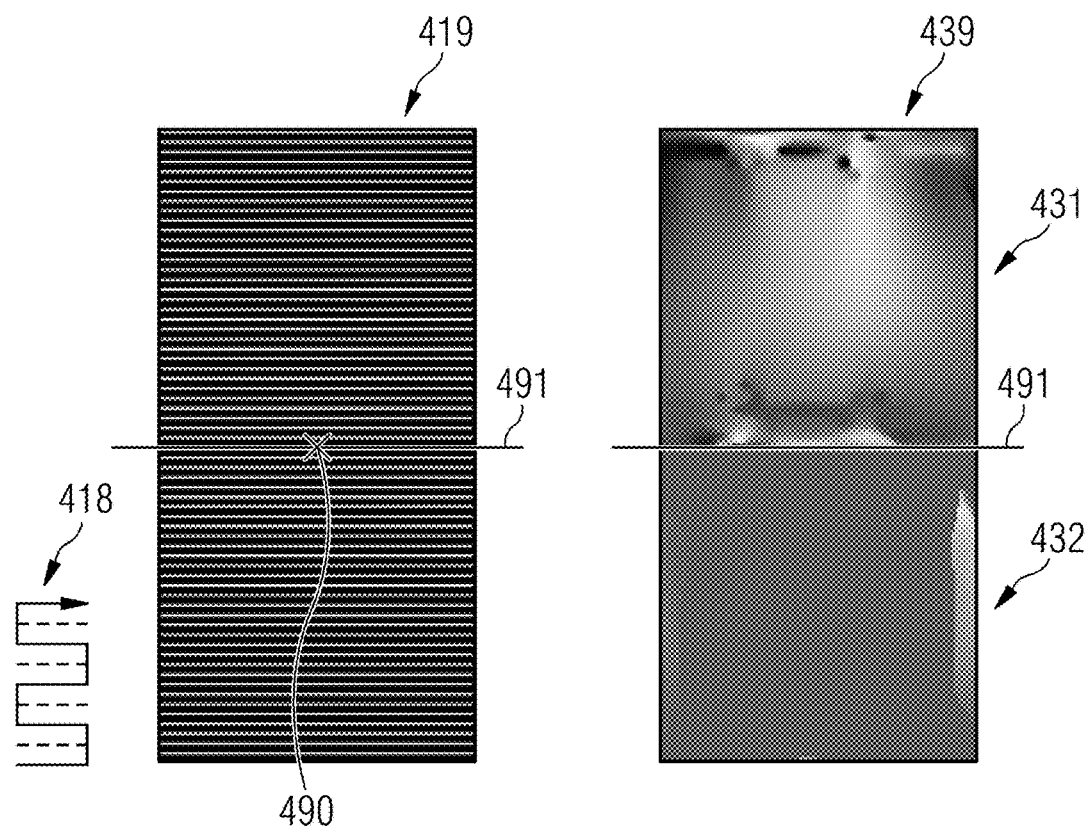
FIG. 5 schematically illustrates an example measurement data structure and an example coil sensitivity data structure determined based on the k-space data the coil sensitivity maps of the example of FIG. 4 according to various embodiments of the present disclosure.

Aspects with respect to box 3010 and 3020 are illustrated in FIG. 4 and FIG. 5.

FIG. 4 schematically illustrates example multiple coil sensitivity maps associated with a receiver coil, as well as example k-space data associated with the receiver coil according to various embodiments of the present disclosure. FIG. 4 illustrates the k-space trajectory 411 (using Cartesian sampling along the phase encoding direction 481 and the readout direction 482) used to acquire k-space data 412 (in FIG. 4 and FIG. 5, the white lines are not sampled, and the black lines are sampled).

Also illustrated are two CSMs 431, 432 determined for a given coil of the receiver coil array. The first order CSMs 431 include information regarding the sensitivity of the respective receiver coil in the FOV, whereas the second order CSMs 432 include wrap-in information from outside of the FOV.

FIG. 5 schematically illustrates an example measurement data structure and an example coil sensitivity data structure determined based on the k-space data the coil sensitivity maps of the example of FIG. 4 according to various embodiments of the present disclosure. FIG. 5 illustrates the adjusted k-space trajectory 418. The adjusted k-space trajectory is obtained by stretching, by a stitching factor of two corresponding to the count of CSMs per coil, the k-space trajectory 411 along the phase-encoding direction 481. The stretching is symmetrical with respect to the axis 491 that includes the k-space center 490, i.e. the position of the k-space center 490 is preserved.

Note that the stretching of the k-space trajectory 411 to obtain the adjusted k-space trajectory 418 can be seen of changing the acceleration factor from 2 to 4, i.e. for a larger FOV the same number of k-space data samples are obtained.

The k-space data is re-arranged in accordance with the adjusted k-space trajectory 418, and the respective measurement data structure 419 is obtained.

Also illustrated in FIG. 5 is the coil sensitivity data structure 439 that is obtained from stitching along the phase-encoding direction 481, the CSMs 431, and the CSM 432.

The measurement data structure 419 and the coil sensitivity data structure 439 of the same dimensions.

Now referring again to FIG. 3, in box 3025, an MRI image is reconstructed using a SENSE reconstruction that is, as input data, operating based on the measurement data structure 419 and the coil sensitivity data structure 439.

Here, the regularization operation usually does not have the same boundary conditions as the Fourier transform. This can lead to artifacts. However, most MR applications assume air at the boundary of the PE direction, so that artifacts would be meaningless at the boundary (only showing background).

At optional box 3030, it would be possible to crop the reconstructed MRI image to the area of the first order CSMs (cf. FIG. 4: CSM 431).

Although the disclosure has been shown and described with respect to certain preferred embodiments, equivalents and modifications will occur to others skilled in the art upon the reading and understanding of the specification. The present disclosure includes all such equivalents and modifications and is limited only by the scope of the appended claims.

For illustration, the techniques could be extended to simultaneous multi-slice reconstruction. For example, techniques are known for simultaneously exciting nuclear magnetization in multiple slices of the examination region and for simultaneously acquiring MR data from that number of slices. Such techniques are frequently called simultaneous multislice (SMS) imaging. See for example Setsompop, Kawin et al. "Blipped controlled aliasing in parallel imaging for simultaneous multislice echo planar imaging with reduced g-factor penalty." Magnetic resonance in Medicine 67 (2012) 1210-1224. Also, see Barth, Markus, et al. "Simultaneous multislice (SMS) imaging techniques." Magnetic resonance in medicine 75.1 (2016): 63-81. Conventionally, to separate or disentangle the totality of MR data in k-space into datasets for respective slices, a technique of the type developed for parallel imaging (partial parallel acquisition, PPA) is used, which has a slice-specific reconstruction kernel for each of the slices.

The techniques could be further used for three-dimensional acquisition or three-dimensional plus time-resolved acquisition.

For still further illustration, above, various scenarios have been disclosed in which the CSMs of higher rank are determined for a given FOV for which also the k-space data is acquired using an undersampling trajectory. This means that the higher-order CSMs include wrap-in information from outside that FOV. In some scenarios, it would also be possible that only a single CSM is determined for each coil of the receiver coil array using an autocalibration protocol that densely samples a part of the k-space for a first FOV. Then, for each coil of the receiver coil array, it would be possible to acquire K-space data using an undersampling trajectory in the k-space for a second FOV that is an integer fraction of the first FOV. That is, the second FOV could be smaller by a factor of two or three, etc., than the first FOV. It is then possible to determine, for each coil, a respective measurement data structure including the respective k-space data rearranged in the k-space on an adjusted k-space trajectory that is determined by stretching the k-space trajectory by the inverse of the integer fraction (here, by a factor of two or three etc.).

For instance, as explained above in connection with FIG. 4 and FIG. 5, a stretching by a factor of two would be possible where the FOV for which the autocalibration protocol densely samples the part of the k-space is larger by the same factor of two than the FOV for which the measurement data is acquired. Also by such techniques, the same dimensions can be obtained for the CSMs and the measurement data structure, as explained in connection with FIG. 5 for the coil sensitivity data structure and the measurement data structure. However, instead of having two separate CSMs that are stitched together, wherein one of those two CSMs includes warp-in information from outside the FOV, only a single CSM for a larger FOV is obtained. This CSM natively includes information corresponding to the wrap-in information. Then, it would be possible that such CSM and the measurement data structure is fed, as input data, to the sense reconstruction algorithm.

Although the disclosure has been illustrated and described in detail using the preferred exemplary embodiments, the disclosure is not limited by the disclosed examples, and a person skilled in the art can derive other variations therefrom without departing from the scope of protection of the disclosure The various components described herein may be referred to as "units." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units, as applicable and relevant, may alternatively be referred to herein as "circuitry," "controllers," "processors," or "processing circuitry," or alternatively as noted herein.

What is claimed is:

1. A computer-implemented method of reconstructing magnetic resonance imaging (MRI) images, the method comprising:
   for each coil of a receiver coil array of an MRI apparatus, determining a respective set of two or more coil sensitivity maps using an autocalibration protocol comprising an Eigenvalue-based Spatially Constrained Iterative Reconstruction Technique (ESPIRIT) autocalibration protocol densely sampling a part of k-space and determining a respective coil sensitivity data structure comprising the respective two or more coil sensitivity maps in a stitched arrangement along a predetermined direction in k-space, a stitching factor of the stitched arrangement corresponding to a number of the two or more coil sensitivity maps of the respective set,
   for each coil of the receiver coil array, acquiring k-space data using an undersampling trajectory in k-space, and determining a respective measurement data structure comprising respective k-space data rearranged in k-space on an adjusted undersampling k-space trajectory that is determined by stretching the undersampling trajectory in k-space by the stitching factor along the predetermined direction, and
   based on the coil sensitivity data structures determined for the coils of the receiver coil array, and further based on the respective measurement data structures determined for the coils of the receiver coil array, performing an iterative optimization based on a SENSitivity Encoding (SENSE) reconstruction algorithm to obtain at least one MRI image,
   wherein the iterative optimization comprises, for at least a portion of iterations of multiple iterations of the iterative optimization, a regularization operation and a data-consistency operation, and
   wherein the data-consistency operation is based on differences between the measurement data structures and respective synthesized measurement data structures, the synthesized measurement data structures being based on a k-space representation of at least one prior MRI image of the multiple iterations, the adjusted undersampling k-space trajectory, and the coil sensitivity data structures.

2. The computer-implemented method of claim 1, wherein the iterative optimization is implemented by a reconstruction algorithm that is configured to accept, as input data, the coil sensitivity data structures and the measurement data structures for a predetermined range of stitching factors.

3. The computer-implemented method of claim 2, wherein the reconstruction algorithm is configured to further accept, as the input data, non-stitched coil sensitivity maps and k-space data that is not rearranged in k-space.

4. The computer-implemented method of claim 1, wherein k-space data is acquired for each coil at multiple echo times to thereby obtain two or more MRI images for two or more spin species, and further comprising:
   for each coil of the receiver coil array: augmenting the respective coil sensitivity data structure by combining the respective coil sensitivity data structure with predetermined dephasing maps obtained for each one of the multiple echo times and at least one predetermined dephasing factor associated with a relative dephasing between at least one pair of the two or more spin species.

5. The computer-implemented method of claim 1, wherein the regularization operation is implemented by multiple layers of a convolutional neural network, different ones of the multiple layers being associated with different ones of the multiple iterations.

6. The computer-implemented method of claim 1, wherein the undersampling trajectory comprises sampling points arranged on a Cartesian pattern in k-space along the predetermined direction.

7. The computer-implemented method of claim 6, wherein the sampling points of the undersampling trajectory in k-space are arranged on a non-Cartesian pattern in k-space along at least one further direction that is perpendicular to the predetermined direction.

8. The computer-implemented method of claim 1, wherein the undersampling trajectory in k-space comprises sampling points arranged in k-space in accordance with a stack-of-stars or a stack-of-spirals pattern.

9. The computer-implemented method of claim 1, wherein the predetermined direction is a phase-encoding direction of a measurement protocol used to acquire the k-space data.

10. The computer-implemented method of claim 1, wherein the predetermined direction is a readout direction of a measurement protocol used to acquire the k-space data.

11. The computer-implemented method of claim 1, wherein the stretching is symmetrical about an axis perpendicular to the predetermined direction and comprises a center of k-space.

12. The computer-implemented method of claim 1, wherein:
the autocalibration protocol densely samples the part of the k-space for a predetermined field-of-view,
the k-space data is acquired using the undersampling trajectory in k-space for the same predetermined field-of-view, and
at least one of the two or more coil sensitivity maps of a set associated with a predetermined coil of the receiver coil array comprises wrap-in information from outside the predetermined field-of-view.

13. The computer-implemented method of claim 1, wherein the stitching factor is two.

14. A computer-implemented method of reconstructing magnetic resonance imaging (MRI) images, the method comprising:
for each coil of a receiver coil array of an MRI apparatus, determining a respective coil sensitivity map using an autocalibration protocol comprising an Eigenvalue-based Spatially Constrained Iterative Reconstruction Technique (ESPIRIT) autocalibration protocol densely sampling a part of k-space for a first field-of-view,
for each coil of the receiver coil array of the MRI apparatus, acquiring k-space data using an undersampling trajectory in k-space for a second field-of-view that is an integer fraction of the first field-of-view, and determining a respective measurement data structure comprising the respective k-space data rearranged in k-space on an adjusted undersampling k-space trajectory that is determined by stretching the undersampling trajectory in k-space by an inverse of the integer fraction, and
based on the respective coil sensitivity maps determined for the coils of the receiver coil array, and further based on the respective measurement data structures determined for the coils of the receiver coil array, performing an iterative optimization based on a SENSitivity Encoding (SENSE) reconstruction algorithm to obtain at least one MRI image,
wherein the iterative optimization comprises, for at least a portion of iterations of multiple iterations of the iterative optimization, a regularization operation and a data-consistency operation to obtain respective current MRI images, and
wherein the data-consistency operation is based on differences between the measurement data structures and respective synthesized measurement data structures, the synthesized MRI measurement data structures being based on a k-space representation of at least one prior MRI image of the multiple iterations, the adjusted undersampling k-space trajectory, and the coil sensitivity maps.

* * * * *